(12) United States Patent
Charles

(10) Patent No.: US 11,883,096 B2
(45) Date of Patent: Jan. 30, 2024

(54) ADAPTIVE OPTICS SYSTEMS AND METHODS FOR VITREORETINAL SURGERY

(71) Applicant: Alcon Inc., Fribourg (CH)

(72) Inventor: Steven T. Charles, Memphis, TN (US)

(73) Assignee: Alcon Inc., Fribourg (CH)

( * ) Notice: Subject to any disclaimer, the term of this patent is extended or adjusted under 35 U.S.C. 154(b) by 637 days.

(21) Appl. No.: 16/941,324

(22) Filed: Jul. 28, 2020

(65) Prior Publication Data

US 2021/0038067 A1 Feb. 11, 2021

Related U.S. Application Data

(60) Provisional application No. 62/883,293, filed on Aug. 6, 2019.

(51) Int. Cl.
*A61B 3/00* (2006.01)
*G02B 27/00* (2006.01)

(52) U.S. Cl.
CPC ............ *A61B 3/005* (2013.01); *A61B 3/0025* (2013.01); *G02B 27/0062* (2013.01)

(58) Field of Classification Search
CPC ......... A61B 3/005; A61B 3/0025; A61B 3/13; A61B 3/145; A61B 3/1015; A61B 90/361; G02B 27/0062

USPC ........................................................ 351/221
See application file for complete search history.

(56) References Cited

U.S. PATENT DOCUMENTS

| | | | |
|---|---|---|---|
| 5,471,515 A | 11/1995 | Fossum | |
| 10,413,179 B2* | 9/2019 | Wang | A61B 3/113 |
| 10,602,926 B2* | 3/2020 | Wang | A61B 3/14 |
| 10,799,115 B2* | 10/2020 | Wang | A61B 3/0091 |
| 2005/0107688 A1* | 5/2005 | Strommer | A61B 5/7475 |
| | | | 600/424 |
| 2013/0242060 A1* | 9/2013 | Brady | H04N 13/204 |
| | | | 348/47 |
| 2016/0124221 A1 | 5/2016 | Huang | |
| 2016/0345820 A1* | 12/2016 | Frisken | A61B 3/0025 |

FOREIGN PATENT DOCUMENTS

| | | |
|---|---|---|
| WO | 2010058199 A1 | 5/2010 |
| WO | 2013165689 A1 | 11/2013 |

* cited by examiner

*Primary Examiner* — Mohammed A Hasan

(57) ABSTRACT

The present disclosure provides an adaptive optics system including at least one active pixel sensor array that detects light and sends a signal to a processor. The adaptive optics system also includes a wavefront correction system including at least one wavefront control structure and the processor, and that executes instructions on the processor to produce a digital image in which at least one wavefront distortion in the light detected by the active pixel sensor array is partially or fully corrected. The disclosure also provides methods of using the adaptive optics system.

18 Claims, 9 Drawing Sheets

ADAPTIVE OPTICS SYSTEMS AND METHODS FOR VITREORETINAL SURGERY

TECHNICAL FIELD

The present disclosure relates to vitreoretinal surgery and surgical equipment, and more specifically, to an adaptive optics system to improve a digital image during vitreoretinal surgery and associated methods.

BACKGROUND

Ophthalmic surgery is surgery performed on the eye or any part of the eye. Ophthalmic surgery saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

One type of ophthalmic surgery, vitreoretinal surgery, encompasses various delicate procedures involving internal portions of the eye, such as the vitreous humor, the retina, epiretinal membranes, and internal limiting membrane. Different vitreoretinal surgical procedures are used, sometimes with lasers, to improve visual sensory performance in the treatment of many eye diseases, including epimacular membrane, diabetic retinopathy, vitreous hemorrhage, macular hole, detached retina, vitreomacular traction syndrome, macular schisis, and complications of cataract surgery, among others.

During ophthalmic surgery, such as vitreoretinal surgery, an ophthalmologist typically uses a non-electronic, optical, surgical microscope with oculars to view a magnified image of the eye undergoing surgery. More recently, vitreoretinal surgeons may use an ocular-free digital image system to aid visualization during vitreoretinal surgery. These systems may include a 3D high dynamic range ("HDR") camera system with a pair of 2D complementary metal-oxide-semiconductor (CMOS) single chip or three-chip sensors that allows the surgeon to view the retina on a display screen using polarized glasses, digital oculars or a head-mounted display. The display screen provides relief from having to view the surgery using oculars and allows others in the operating room to see exactly as the surgeon does. The system also allows for improved images under high magnification, and increased depth of field compared to a conventional optical, analog surgical microscope, which allow for improved visualization of the eye.

SUMMARY

The present disclosure provides an adaptive optics system that improves a digital image during vitreoretinal surgery. The adaptive optics system includes at least one active pixel sensor array that detects light and sends a signal to a processor. The adaptive optics system also includes a wavefront correction system including at least one wavefront control structure and the processor, and that executes instructions on the processor to produce a digital image in which at least one wavefront distortion in the light detected by the active pixel sensor array is partially or fully corrected.

The adaptive optics system and its methods of use may include the following additional features: i) the system may include a plurality of active pixel sensor arrays; ii) the wavefront control structure may include a spatial light modulator (SLM), a liquid crystal on silicon spatial light modulator (LCoS-SLM), a transmissive LCoS-SLM, a reflective LCoS-SLM, a deformable mirror, or any combination thereof; iii) the wavefront control structure may include a phase-only SLM; iv) the digital image may be displayed on a digital display, a screen, a head up display, a head mounted display, or any combination thereof; v) the system may be a component of NGENUITY® (Novartis AG Corp., Switzerland); vi) the active pixel sensor array may be a CMOS monochrome sensor, a 4K monochrome CMOS sensor, a 1080P monochrome CMOS sensor, or any combination thereof; vii) the system may include an on-chip processor on the active pixel sensor array that implements a region of interest (ROI) gain control; viii) the system may include an amplitude-only SLM to implement a ROI gain control on the active pixel sensor array; ix) the system may include an image reference system; x) the image reference system may include an image reference that is a surgical tool placed in an eye; xi) the surgical tool placed in the eye may be a vitreous cutter, forceps, scissors, a pic, a scraper, a flex loop, a spatula, a micro-vitreoretinal (MVR) blade, a microcannula or any combination thereof.

The present disclosure further provides an adaptive optics system that includes a time sequential color system that includes a red light source, a green light source, and a blue light source that emit a sequence of red, green, and blue light spaced over time. The system also includes at least one active pixel sensor array that detects each of the red, green, and blue light, and sends a signal to the processor. The system may include the following additional features: i) the time sequential color system may include a red light emitting diode (LED), a green LED, and a blue LED pulsed in sequence at an aggregate rate of 180 Hz or above; ii) time sequential color system may include a red superluminescent light emitting diode (SLED), a green SLED, and a blue SLED pulsed in sequence at an aggregate rate of 180 Hz or above; iii) the time sequential color system may be delivered by an endoilluminator; iv) the active pixel sensor array may be an active pixel sensor array without a Bayer filter; v) the active pixel sensor array may capture sequentially a red image, a green image, and a blue image.

The present disclosure further provides a medical system that includes a processor, at least one active pixel sensor array that is coupled to the processor, a wavefront correction system that is coupled to the processor, an image reference system, and a memory medium that is coupled to the processor. The memory medium includes instructions that, when executed by the processor, cause the medical system to utilize the image reference system to determine a wavefront distortion of a reflected wavefront of light reflected off an interior of an eye of a patient. The memory medium further includes instructions that, when executed by the processor, cause the medical system to utilize the wavefront correction system to correct the wavefront distortion of the reflected wavefront of light reflected off the interior of the eye.

The present disclosure further provides a method of correcting a wavefront distortion to improve a digital image by using an image reference system to determine a wavefront distortion of a reflected wavefront of light reflected off the interior of the eye; and using a wavefront correction system to correct the wavefront distortion of the reflected wavefront of light reflected off the interior of eye. The present disclosure also provides a method of eliminating lateral color spread and improving color rendition to improve a digital image by using a time sequential color system emitting a sequence of a red light, a green light, and a blue light spaced over time to illuminate the interior of the eye; detecting a red wavefront of light, a green wavefront of light, and a blue wavefront of light reflected off the interior of the eye using at least one active pixel sensor array without a Bayer filter; capturing a red image, a green image, and a blue image of the interior of the eye sequentially using the active pixel sensor array without a Bayer filter; and integrating the red image, the green image, and the blue image in the viewer's visual cortex, or reformatting the red image, the green image, and the blue image for an organic light-emitting diode (OLED) display, to give a color image of the interior of the eye with lateral color spread eliminated.

Aspects of the adaptive optics system and its methods of use may be combined with one another unless clearly mutually exclusive. In addition, the additional features of the adaptive optics system and its associated methods described above may also be combined with one another unless clearly mutually exclusive.

BRIEF DESCRIPTION OF THE DRAWINGS

For a more complete understanding of the present disclosure and its features and advantages, reference is now made to the following description, taken in conjunction with the accompanying drawings, which are not to scale, in which like numerals refer to like features, and in which.

DETAILED DESCRIPTION

Figure 1:
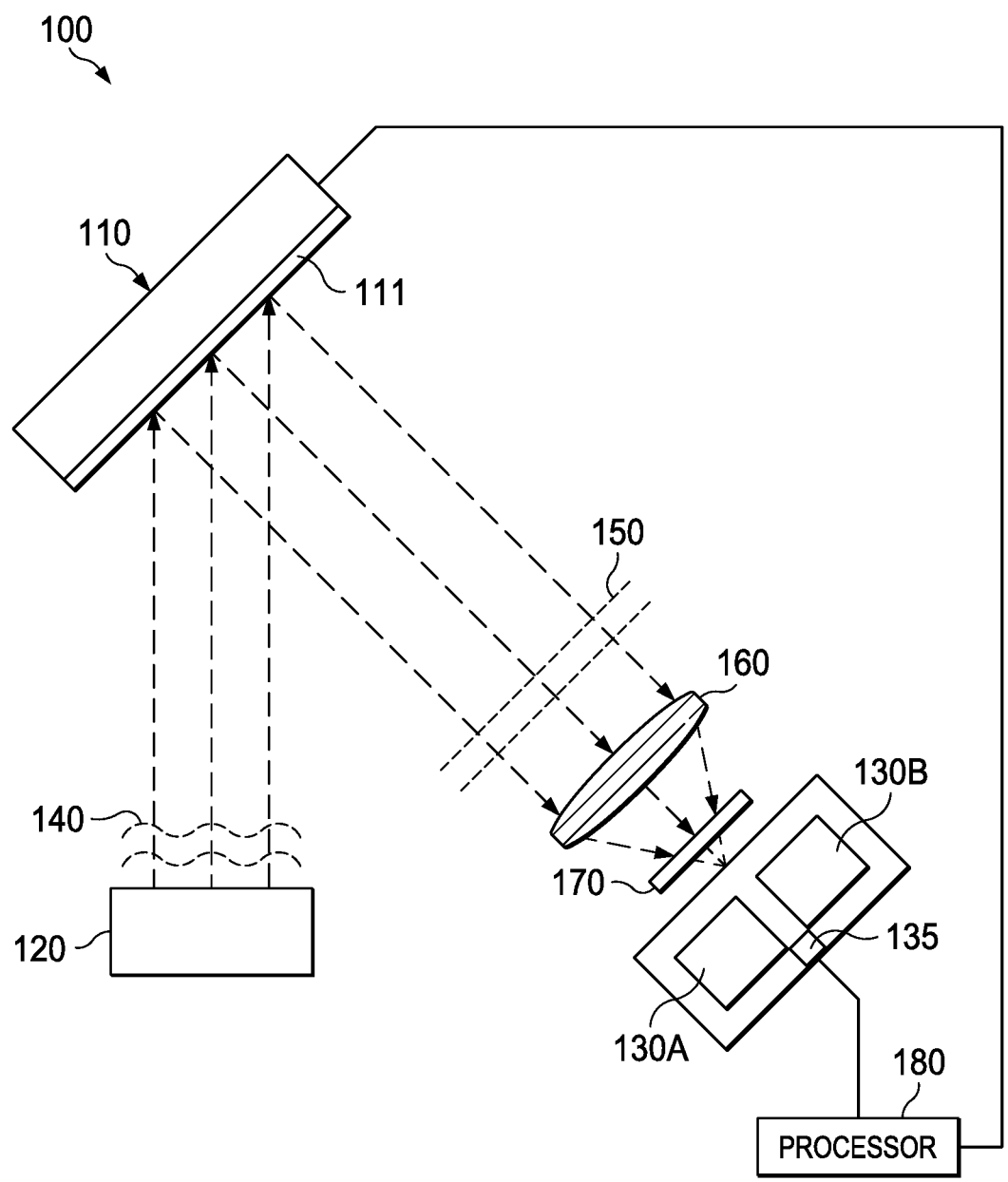
FIG. 1 is a schematic representation of an adaptive optics system, including a wavefront correction system, a time sequential color system, and two monochrome active pixel sensor arrays.

The present disclosure provides systems including adaptive optics to improve a digital image for vitreoretinal surgery and associated methods.

Vitreoretinal surgeons face unique challenges when visualizing the internal portions of the eye. For example, any view obtained through the patient's pupil is subject to optical aberration. Optical aberration may be caused by eye diseases or prior surgery causing corneal asphericity or intraocular lens implants which lead to an aberrated image viewed by the surgeon. Spherical aberration may be caused by dilation of the pupil, oblique viewing to visualize the peripheral retina, cataract, intraocular lenses, and corneal asphericity. Chromatic aberration, which may be lateral or axial, may be caused by the failure of the eye's optical system or retinal visualization system to focus different colors to the same focal point or plane. Aberration may interfere with the ability of the surgeon to visualize the interior of the eye and make surgery more difficult. In analog systems there are very limited ways to correct for the effect of aberrations, and many are simply uncorrectable. However, digital visualization systems do allow for various corrective measures as described herein, which may improve the image presented to the surgeon and others assisting with vitreoretinal surgery.

In particular, the systems and methods disclosed herein may reduce the effects of aberrations in a digital image of the eye seen by the surgeon and others. By doing so, the systems and methods may reduce aberration and improve digital image resolution, digital image color rendition, digital image dynamic range, or any combinations thereof during visualization in any aspects of vitreoretinal surgery. Systems and methods of the present disclosure may improve a digital image for vitreoretinal surgery as compared to current systems and methods by including an adaptive optics system that may reduce spherical aberration or chromatic aberration, reduce aberration from defocus caused by myopia and hyperopia, regular astigmatism, coma, or trefoil, eliminate lateral color spread, allow region of interest ("ROI") gain control, or any combinations thereof.

Current systems and methods for digital visualization during vitreoretinal surgery do not include an adaptive optics system. Instead, they rely on a twin sensor high dynamic range camera system, where the effects of aberration may manifest as wavefront distortion, leading to image distortion, and reduced image quality. Wavefront distortion in vitreoretinal surgery may also be caused by retinal visualization systems (for example, macular or wide-angle contact lenses, or non-contact viewing systems such as BIOM® (OCULUS Surgical, Inc., USA) and ReSight® (Carl Zeiss Meditec AG, Germany)), or corneal asphericity that may result from photorefractive keratectomy (PRK), laser-assisted in situ keratomileusis (LASIK), penetrating keratoplasty (PK), radial keratotomy (RK), limbal relaxing incision (LRI), Descemet membrane endothelial keratoplasty (DMEK), Descemet' s stripping endothelial keratoplasty (DSEK), anterior lamellar keratoplasty (ALK), inlays, trauma, keratoconus, or pterygium. Wavefront distortion in vitreoretinal surgery may alternatively be caused by tilt due to oblique viewing angle to see the peripheral retina, a dilated pupil, a crystalline lens with or without a cataract, an intraocular lens (especially multifocal or extended depth of focus intraocular lenses), or corneal astigmatism in aphakic eyes. Current adaptive optics systems used in ophthalmic research are typically very high magnification, non-stereo, monochromatic, not real time, have a very small field of view, require a minimally-moving subject, and are not suitable for surgery. The adaptive optics system to improve a digital image for vitreoretinal surgery as described herein may utilize broadband white light, work in real time, display stereo images, have no apparent latency, and provide the same magnification as current surgical microscopes and state-of-the-art Digitally Assisted Vitreoretinal Surgery ("DAVS") system NGENUITY® (Novartis AG Corp., Switzerland).

The adaptive optics system described herein may correct wavefront distortion to improve a digital image for vitreoretinal surgery by including a wavefront correction system. The wavefront correction system may include a wavefront control structure that controls and corrects wavefront distortion resulting in reflected light with a corrected wavefront. The wavefront control structure may be a deformable mirror, where the surface of the mirror may be deformed to control and correct wavefront distortion. The wavefront control structure may also be a spatial light modulator ("SLM"). The SLM may be a pixelated device that modulates phase, or polarization of light waves. The SLM may be used for wavefront shaping by controlling the phase of incident light at each pixel. SLMs have a much higher resolution compared to deformable mirrors thereby enabling complex wavefront shaping, point spread function engineering, and pixel engineering that may reduce the effects of aberration. The wavefront control structure may be a phase-only SLM. The wavefront control structure may also be a liquid crystal on silicon SLM ("LCoS-SLM"), may be a transmissive LCoS-SLM, or may be a reflective LCoS-SLM. Wavefront shaping by the SLM may correct wavefront distortion and reduce the effects of aberration, which may be spherical aberration, to improve a digital image.

In the adaptive optics system described herein, a wavefront correction system may be utilized in conjunction with a time sequential color system. The time sequential color system provides a red light source, a green light source, and a blue light source, which may emit a sequence of red, green, and blue light spaced over time. The red light, green light, and blue light sources may be pulsed in sequence at an aggregate rate above 180 Hz to avoid color flicker or color breakup. The time sequential color system provides red, green, and blue light, and may illuminate the eye during surgery. The red light, green light, and blue light sources may be delivered by an endoilluminator, which is a fiberoptic probe inserted through the pars plana. Wavefront distortion from the red light, green light, and blue light delivered by the endoilluminator and reflected by the eye may be corrected by the wavefront correction system. The implementation of a wavefront correction system and a time sequential color system in the same adaptive optics system may allow different wavefront shaping or transform for each of the red, green, and blue light sources, which may reduce chromatic aberration in a digital image by focusing red, green, and blue colors to the same convergence point or image plane. This may reduce lateral chromatic aberration, axial chromatic aberration, or a combination thereof.

Alternatively, the time sequential color system may utilize at least one light source that is a color other than red, green, or blue. The time sequential color system may also utilize at least three light sources that may be colors of different wavelengths.

The adaptive optics system to improve a digital image for vitreoretinal surgery described herein may use an image reference to improve the digital image of the eye. The image reference may be used in a similar way as a guide star is used in adaptive optics systems for astronomy.

Generally, an image reference may be a reference object with a known shape that is placed in the eye. In the adaptive optics system described herein, a surgical tool may be used as an image reference. The surgical tool may be a vitreous cutter, forceps, scissors, a pic, a scraper, a flex loop, a spatula, a MVR blade, a micro-cannula or any combination thereof. If the shape of the surgical tool is not known before use, a non-aberrated image of the surgical tool may be created outside of the eye before the surgical tool is placed in the eye. This may allow the same surgical tool when placed internally in the eye during surgery to be used as an image reference. The wavefront distortions in the view pathway, which may be in reflected light from the endoilluminator, may be corrected using the wavefront correction system to restore an image of the image reference to its non-aberrated appearance, which may be the non-aberrated image of the surgical tool. The light may come from a time sequential color system delivered by an endoilluminator. A processor may analyze the wavefront distortions in the digital image of the image reference and send instructions to the wavefront correction system to control and correct the wavefront distortions to improve the digital image of the image reference. The same instructions may be used to control and correct the wavefront distortions in the light reflected off the eye to improve the digital image of the eye. In this example, a Shack-Hartmann wavefront sensor may not be utilized.

The adaptive optics system to improve a digital image for vitreoretinal surgery described herein may include an active pixel sensor array, which is a light sensor array that detects light and conveys the information used to make a digital image. An active pixel sensor array may be an array of light-capturing cells, typically with each cell representing a pixel. A pixel in an active pixel sensor array may detect only brightness information, and no color information. A color filter called a Bayer filter may be used to allow an active pixel sensor array to function as a color sensor. A Bayer filter applies a red, green, or blue filter to each pixel, and may be placed in front of the active pixel sensor array. The Bayer filter allows the correct brightness and color information to be calculated for each pixel, and may result in a color digital image. The adaptive optics system described herein may include a single active pixel sensor array. The active pixel sensor array may include left and right channels to provide a 3D stereo image. Alternatively the adaptive optics system may include two active pixel sensor arrays, or may include multiple active pixel sensor arrays. A 3D stereo image may also be provided using a pair of active pixel sensor arrays.

The active pixel sensor array in the adaptive optics system may include a Bayer filter, or may be an active pixel sensor array without a Bayer filter. The Bayer filter may introduce lateral color spread into a digital image for vitreoretinal surgery, which may lead to decreased color rendition. In the adaptive optics system described herein, the inclusion of a time sequential color system may allow the active pixel sensor array to capture sequentially a red image, a green image, and a blue image. The red image, the green image, and the blue image may be integrated in the viewer's visual cortex to give a color image of the eye. Alternatively, the red image, the green image, and the blue image may be processed electronically by an image processor and reformatted for an OLED display, digital oculars or a head-mounted display. This may remove the need for a Bayer filter on the active pixel sensor array to obtain a color image. Therefore, the adaptive optics system described herein may be used for color visualization using an active pixel sensor array without a Bayer filter but with a time sequential color system, which may reduce lateral color spread on the active pixel sensor array and increase color rendition in a digital image for vitreoretinal surgery.

The adaptive optics system for an improved digital image in vitreoretinal surgery in the present disclosure may further include an on-chip processor on the active pixel sensor array, which may implement a region of interest (ROI) gain control to improve dynamic range. ROI gain control may also be implemented by including an additional amplitude-only SLM to improve dynamic range. The amplitude-only SLM may be positioned in a focal plane before the active pixel sensor array.

The systems and methods of the present disclosure may provide any combination of numerous advantages over than what is typically provided by general visualization sensors for vitreoretinal surgery, including: (1) improving a digital image for vitreoretinal surgery by improving image resolution through the use of a wavefront correction system to correct wavefront distortion; (2) improving a digital image for vitreoretinal surgery by improving color rendition through the combined use of a time sequential color system and an active pixel sensor array without a Bayer filter; and (3) improving a digital image for vitreoretinal surgery by improving dynamic range through the use of an active pixel sensor array with ROI gain control.

Referring now to FIG. 1, adaptive optics system 100 includes wavefront correction system 110, time sequential color system 120 and active pixel sensor arrays 130a and 130b. Adaptive optics system 100 may correct wavefront distortion 140 to corrected wavefront 150 using wavefront correction system 110 to improve image resolution. Wavefront correction system 110 may include wavefront control structure 111. Wavefront control structure 111 may control and correct the phase of wavefront distortion 140. Wavefront control structure 111 may be a SLM, an LCoS-SLM, a reflective LCoS-SLM, a deformable mirror, or any combination thereof. Wavefront control structure 111 may also be a phase-only SLM, which may correct the phase of a wavefront. Time sequential color system 120 may be a light source for adaptive optics system 100, and may be a red light source, a green light source, and a blue light source that emit a sequence of red, green, and blue light spaced over time. Time sequential color system 120 may include a red light emitting diode (LED), a green LED, and a blue LED that may be pulsed in sequence at an aggregate rate above 180 Hz to avoid flicker. The LEDs may also be or include superluminescent light emitting diodes (SLEDs), which may support nanofiber illuminated tools such as cannulas, cutters, forceps and scissors. Time sequential color system 120 may be delivered by a fiberoptic endoilluminator probe, and red, green, and blue light may be delivered through the pars plana of the eye to be visualized. Wavefront distortion 140 of red light, green light, and blue light delivered by the endoilluminator and reflected by the eye may be corrected by the wavefront correction system 110. In this case, wavefront distortion 140 may be caused by the lens of the eye with or without a cataract, an intraocular lens, the cornea and retinal visualization system after light from the endoilluminator is reflected from the retina, sclera, choroid, the vitreous, scar tissue, epiretinal membrane, internal limiting membrane, hemorrhage or surgical tools. Wavefront correction system 110 may use different wavefront shaping for each of the three light colors red, green and blue emitted by time sequential color system 120, which may reduce axial and lateral chromatic aberration in the adaptive optics system 100. Wavefront correction system 110 may also include processor 180, and may execute instructions on processor 180 to produce a digital image in which at least one wavefront distortion in the light detected by active pixel sensor arrays 130a and 130b is partially or fully corrected.

Active pixel sensor arrays 130a and 130b may detect white light, or may detect each of the red, green, and blue light emitted by time sequential color system 120, and may send a signal to processor 180. In one example, processor 180 may receive one or more analog signals from one or more of pixel sensor arrays 130a and 130b, among others.

The one or more analog signals from the one or more of pixel sensor arrays 130a and 130b may be associated with detected light, which may be reflected off an interior of an eye. The analog signals may include information associated with one or more frequencies of light. In another example, processor 180 may receive one or more digital signals from time sequential color system 120. The one or more digital signals from the one or more of pixel sensor arrays 130a and 130b may be associated with detected light, which may be reflected off the interior of an eye. The digital signals may include information associated with one or more frequencies of light.

Active pixel sensor arrays 130a and 130b may be an array of light capturing cells, typically with each cell representing a pixel. Active pixel sensor arrays 130a and 130b may contain pixels that have a photodetector and an active amplifier. The adaptive optics system 100 may include a single active pixel sensor array, may include two active pixel sensor arrays, or may include multiple active pixel sensor arrays. Light may pass through lens 160 before hitting active pixel sensor arrays 130a and 130b. Active pixel sensor arrays 130a and 130b may be monochrome active pixel sensor arrays, may be complementary metal-oxide-semiconductor (CMOS) sensors, or may be charge-couple device (CCD) sensors. CMOS sensors may be single chip 1080P CMOS sensors, or may be 4K monochrome CMOS sensors. Single chip CMOS color sensors typically make use of a Bayer filter, which is a color filter array that may cause lateral color spread. Active pixel sensor arrays 130a and 130b may include a Bayer filter, or may be active pixel sensor arrays without a Bayer filter. Time sequential color system 120 may eliminate the need for a Bayer filter by active pixel sensor arrays 130a and 130b in order to provide a color digital image by allowing a red image, a green image, and a blue image to be captured sequentially. The use of active pixel sensor arrays without a Bayer filter may eliminate lateral color spread and improve image color rendition. The use of active pixel sensor arrays without a Bayer filter may also enable chromatic aberration correction.

Amplitude-only SLM 170 may implement ROI gain control to improve dynamic range. Amplitude-only SLM 170 may be positioned in the focal plane before active pixel sensor arrays 130a and 130b. Alternatively, on-chip processor 135 on active pixel sensor arrays 130a and 130b may implement a region of interest (ROI) gain control to improve dynamic range. Processor 135 may be an additional processor to processor 180. Processor 135 and processor 180 may be physically separate processors in the adaptive optics system, or may be part of the same processor that performs several functions.

Figure 2:
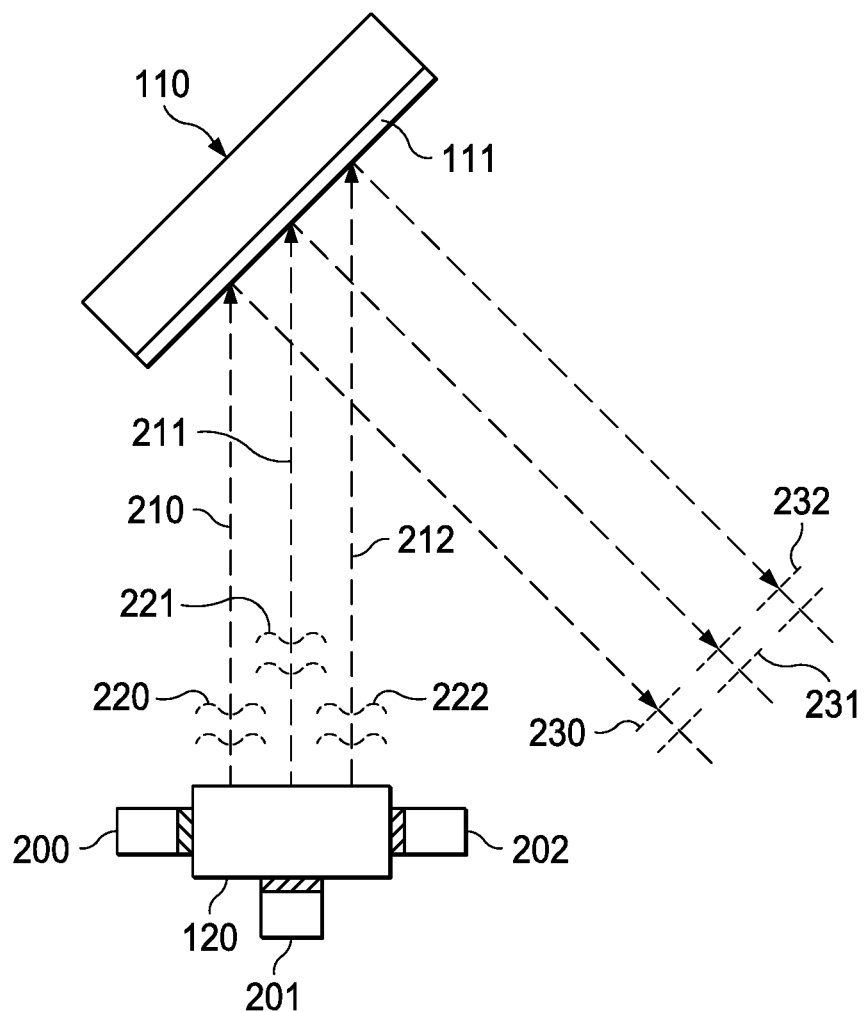
FIG. 2 is a schematic representation of a portion of an adaptive optics system, including a wavefront correction system and a time sequential color system.

The time sequential color system 120 in adaptive optics system 100 may include red light source 200, green light source 201, and blue light source 202, as depicted in FIG. 2. Light sources 200, 201, and 202 may emit a sequence of red, green, and blue light spaced over time. Light sources 200, 201, and 202 may be LEDs, and may be pulsed in sequence at an aggregate rate above 180 Hz to avoid flicker or color breakup. Light sources 200, 201, and 202 may also be SLEDs. Light sources 200, 201, and 202 may be delivered by an endoilluminator, and light may be delivered through the endoilluminator fiberoptic probe through the pars plana of the eye to be visualized. Red light source 200 may emit red light wave 210, which after being reflected by the retina or a surgical tool may have red-light wavefront distortion 220. Green light source 201 may emit green light wave 211, which after being reflected by the retina or a surgical tool may have green-light wavefront distortion 221. Blue light source 202 may emit blue light wave 212, which after being reflected by the retina or a surgical tool may have blue-light wavefront distortion 222. Wavefront correction system 110 may correct wavefront distortion 220, 221, and 222 to corrected red wavefront 230, corrected green wavefront 231, and corrected blue wavefront 232, by performing corrective wavefront shaping. Wavefront shaping by wavefront correction system 110 may be different for each of the wavefront distortions 220, 221, and 222, and may reduce axial and lateral chromatic aberration by ensuring the colors are focused to the same convergence point or image plane.

Figure 3:
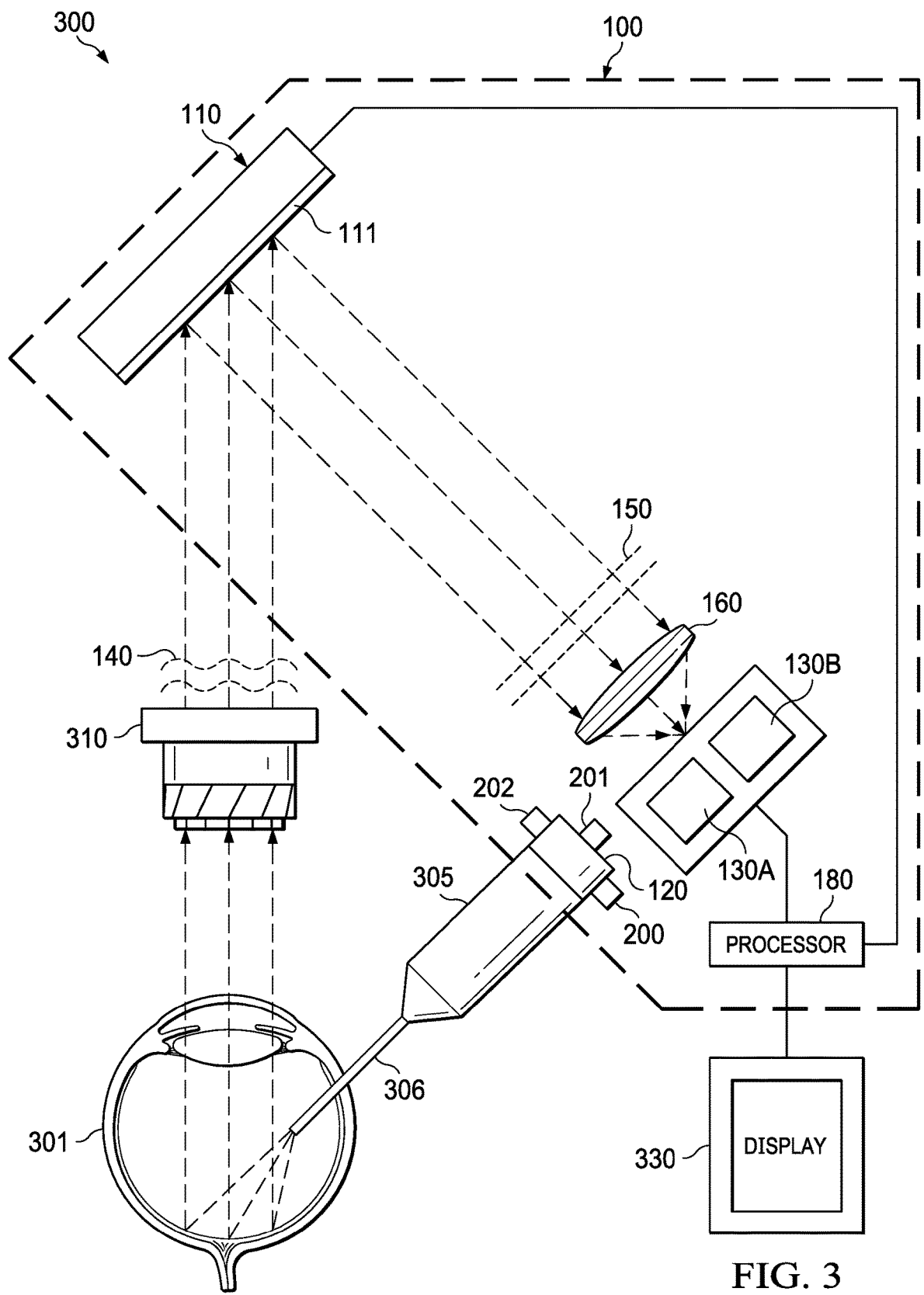
FIG. 3 is a schematic representation of an adaptive optics system as a component of a visualization system.

The adaptive optics system 100 illustrated in FIG. 1 may be a component of a vitreoretinal surgery visualization system 300, as depicted in FIG. 3, to visualize eye 301 during surgery. Visualization system 300 may include a surgical microscope 310, adaptive optics system 100, which may include processor 180, and a digital display 330 such as a screen, a head up display, a head mounted display, or any combination thereof. Digital display 330 may also include multiple displays. Visualization system 300 may be a DAVS system, the NGENUITY® 3D Visualization System (Novartis AG Corp., Switzerland) (FIG. 4), or a camera head mounted on a surgical microscope (FIG. 5).

Visualization system 300 may include time sequential color system 120, which may be a light source for adaptive optics system 100, and may be a red light source, a green light source, and a blue light source that emit a sequence of red, green, and blue light spaced over a period of time. Time sequential color system 120 may be delivered by endoilluminator 305, and red, green, and blue light may be delivered by endoilluminator fiberoptic probe 306 through the pars plana of eye 301. Time sequential color system 120 may illuminate eye 301 using red, green, and blue light sources pulsed in a sequence. For example, time sequential color system 120 may illuminate eye 301 using red, green, and blue light sources pulsed in a sequence with an aggregate rate above 180 Hz, which may be utilized to avoid flicker. Wavefront distortion 140 may be caused by the lens of the eye with or without a cataract, the cornea and contact or non-contact retinal visualization system after light from the endoilluminator is reflected from the retina, sclera, choroid, the vitreous, scar tissue, hemorrhage or surgical tools. Wavefront distortion 140 present in red, green, and blue wavefronts reflected off eye 301 may be corrected by wavefront correction system 110 to reduce the effects of aberration and may improve the digital image resolution of the digital image of eye 301 on digital display 330. Wavefront correction system 110 may include processor 180. Wavefront correction system 110 may execute instructions via processor 180 to produce a digital image. For example, wavefront correction system 110 may produce a digital image in which wavefront distortion 140 in the light detected by active pixel sensor arrays 130a and 130b is partially or fully corrected to corrected wavefront 150.

Active pixel sensor arrays 130a and 130b may be an array of light-capturing cells, typically with each cell representing a pixel, may include a Bayer filter, or may be active pixel sensor arrays without a Bayer filter. Utilization of red, green, and blue light sources in time sequential color system 120 may allow active pixel sensor arrays 130a and 130b to produce color images without a Bayer filter, which may reduce lateral color spread. Lateral color spread in color images produced without a Bayer filter may be reduced compared to lateral color spread in color images produced utilizing a Bayer filter. The reduction in lateral color spread may improve the color rendition of the digital image of eye 301 on digital display 330. Visualization system 300 may include a single active pixel sensor array. Visualization system 300 may include multiple active pixel sensor arrays. Active pixel sensor arrays 130a and 130b may send a signal to processor 180. ROI gain control may be implemented by active pixel sensor arrays 130a and 130b, and may be implemented by an on-chip processor, or an additional amplitude-only SLM. The amplitude-only SLM may be positioned in the focal plane before active pixel sensor arrays 130a and 130b (not shown). ROI gain control implemented by active pixel sensor arrays 130a and 130b may improve the dynamic range of the digital image of eye 301 on digital display 330. Processor 180 may include, for example, a field-programmable gate array (FPGA), a microprocessor, a microcontroller, a digital signal processor (DSP), a graphics processing unit (GPU), an application specific integrated circuit (ASIC), or any other digital or analog circuitry configured to interpret and/or execute program instructions and/or process data.

Processor 180 may include any physical device able to store and/or execute instructions. Processor 180 may execute processor instructions to implement at least a portion of one or more systems, one or more flow charts, one or more processes, and/or one or more methods described herein. For example, processor 180 may execute instructions to produce the image of eye 301. Processor 180 may be configured to receive instructions from a memory medium. In one example, processor 180 may include the memory medium. In another example, the memory medium may be external to processor 180. The memory medium may store the instructions. The instructions stored by the memory medium may be executable by processor 180 and may be configured, coded, and/or encoded with instructions in accordance with at least a portion of one or more systems, one or more flowcharts, one or more methods, and/or one or more processes described herein.

A FPGA may be may be configured, coded, and/or encoded to implement at least a portion of one or more systems, one or more flow charts, one or more processes, and/or one or more methods described herein. For example, the FPGA may be configured, coded, and/or encoded to produce an image of eye 301. An ASIC may be may be configured to implement at least a portion of one or more systems, one or more flow charts, one or more processes, and/or one or more methods described herein. For example, the ASIC may be configured, coded, and/or encoded to produce an image of eye 301. A DSP may be may be configured, coded, and/or encoded to implement at least a portion of one or more systems, one or more flow charts, one or more processes, and/or one or more methods described herein. For example, the DSP may be configured, coded, and/or encoded to produce an image of eye 301.

Although processor 180 is depicted separately from active pixel sensor arrays 130a and 130b, a single device may include processor 180 and active pixel sensor arrays 130a and 130b. In one example, a single computer system may include processor 180 and active pixel sensor arrays 130a and 130b. In another example, a device may include integrated circuits that may include processor 180 and active pixel sensor arrays 130a and 130b.

Processor 180 may interpret and/or execute program instructions and/or process data stored in a memory medium. The memory medium may be configured in part or whole as application memory, system memory, or both. The memory medium may include any system, device, or apparatus configured to hold and/or house one or more memory devices. Each memory device may include any system, any module or any apparatus configured to retain program instructions and/or data for a period of time (e.g., computer-readable media). One or more servers, electronic devices, or other machines described may include one or more similar such processors or memories that may store and execute program instructions for carrying out the functionality of the associated machine.

Surgical microscope 310 may display an image of eye 301, such as a digital image generated by processor 180 or another processor. Surgical microscope 310 may display other information in addition to an image of eye 301. Such other information may be generated by processor 180 or another processor and may include graphic or textual information, such as warnings, graphs, color coding, surgical parameters, endoscopic video, optical coherence tomography (OCT) images, or augmented reality information.

Digital display 330 may similarly display a digital image of eye 301 generated by processor 180 or another processor and other information generated by processor 180 or another processor. Such information may include graphic or textual information, such as surgical parameters, surgical modes, flow rates, intraocular pressure, endoscopic video, OCT images, warnings, digital images, color coding or augmented reality information. The information displayed on digital display 330 may not match that displayed on or seen using surgical microscope 310. Processor 180 may reformat video made using time sequential color system 120 as a light source for display on digital display 330, which may be viewed with circularly polarized glasses, digital oculars, or using a head mounted display.

Visualization system 300 may further contain other elements to facilitate its uses, such as memory to store images displayed on digital display 330, electrical connections, and hardware to position and focus any lenses, such as lens 160, and to position active pixel sensor arrays 130a and 130b.

Figure 4:
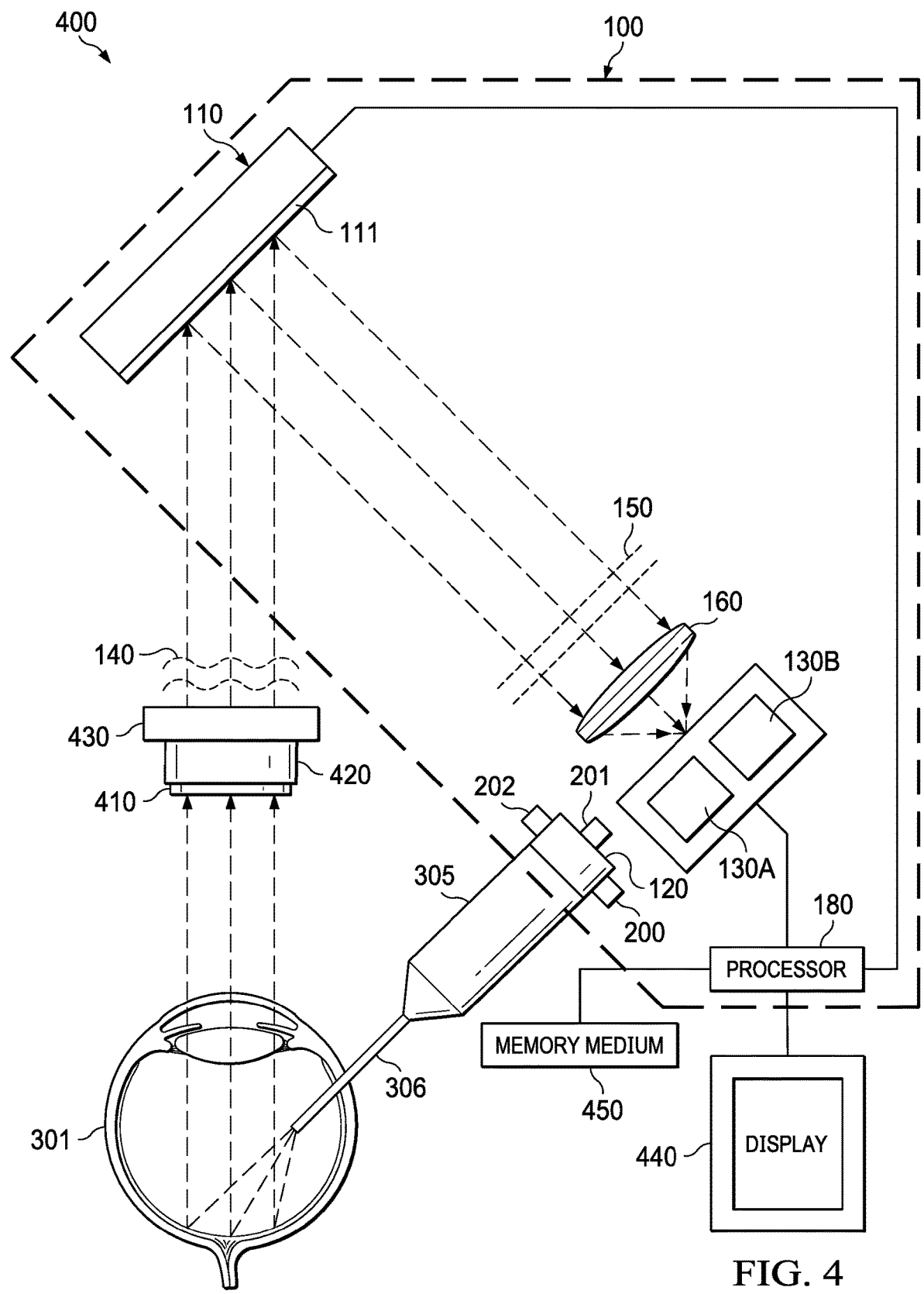
FIG. 4 is a schematic representation of an adaptive optics system as a component of the NGENUITY® 3D Visualization System (Novartis AG Corp., Switzerland)
Figure 5:
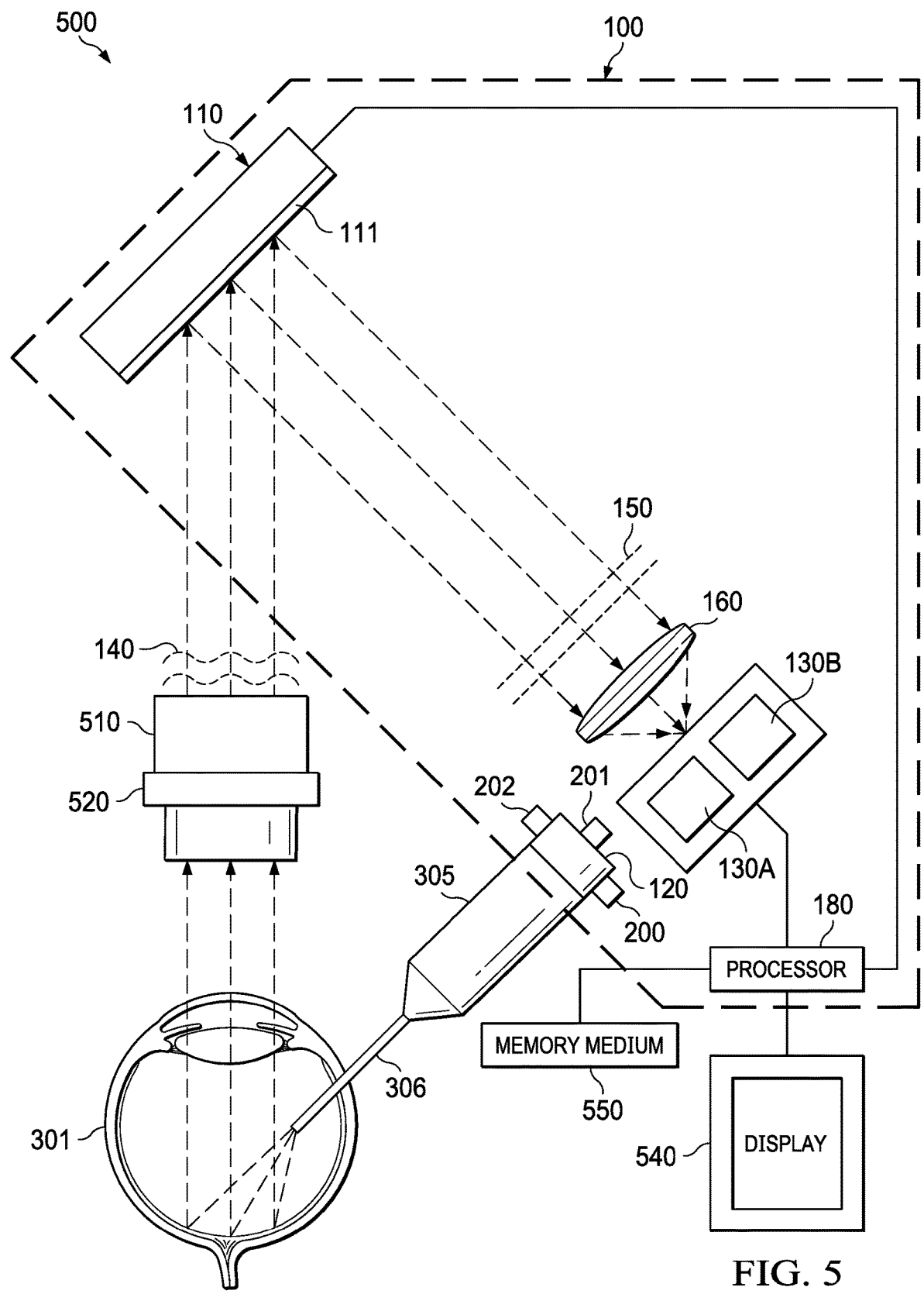
FIG. 5 is a schematic representation of an adaptive optics system as a component of a camera head on a surgical microscope.

Adaptive optics system 100 may be used as a component of the NGENUITY® DSM-1 system (Novartis AG Corp., Switzerland) in visualization system 400, wherein it may replace the sensor portion as depicted in FIG. 4. For example, the adaptive optics system 100 may utilize opto-mechanical focus system 410, zoom system 420, variable working distance system 430, display system 440, and a memory medium 450. In one example, memory medium 450 may store data that may be utilized in implementing at least a portion of one or more systems, one or more flow charts, one or more processes, and/or one or more methods described herein. In another example, memory medium 450 may store instructions executable by processor 180 in implementing at least a portion of one or more systems, one or more flow charts, one or more processes, and/or one or more methods described herein. As illustrated, memory medium 450 may be communicatively coupled to processor 180. As shown, display 440 may be communicatively coupled to processor 180.

Adaptive optics system 100 may be used as a component of a camera head 510 in visualization system 500, which may further include surgical microscope without oculars 520, as depicted in FIG. 5. Visualization system 500 may also include processor 180, and may further include display system 540, and memory medium 550. Camera head 510 may be the NGENUITY® 1.0 (Novartis AG Corp., Switzerland) camera head. In one example, memory medium 550 may store data that may be utilized in implementing at least a portion of one or more systems, one or more flow charts, one or more processes, and/or one or more methods described herein. In another example, memory medium 550 may store instructions executable by processor 180 in implementing at least a portion of one or more systems, one or more flow charts, one or more processes, and/or one or more methods described herein. As shown in FIG. 5, memory medium 550 may be communicatively coupled to processor 180. Display 540 may also be communicatively coupled to processor 180.

Figure 6:
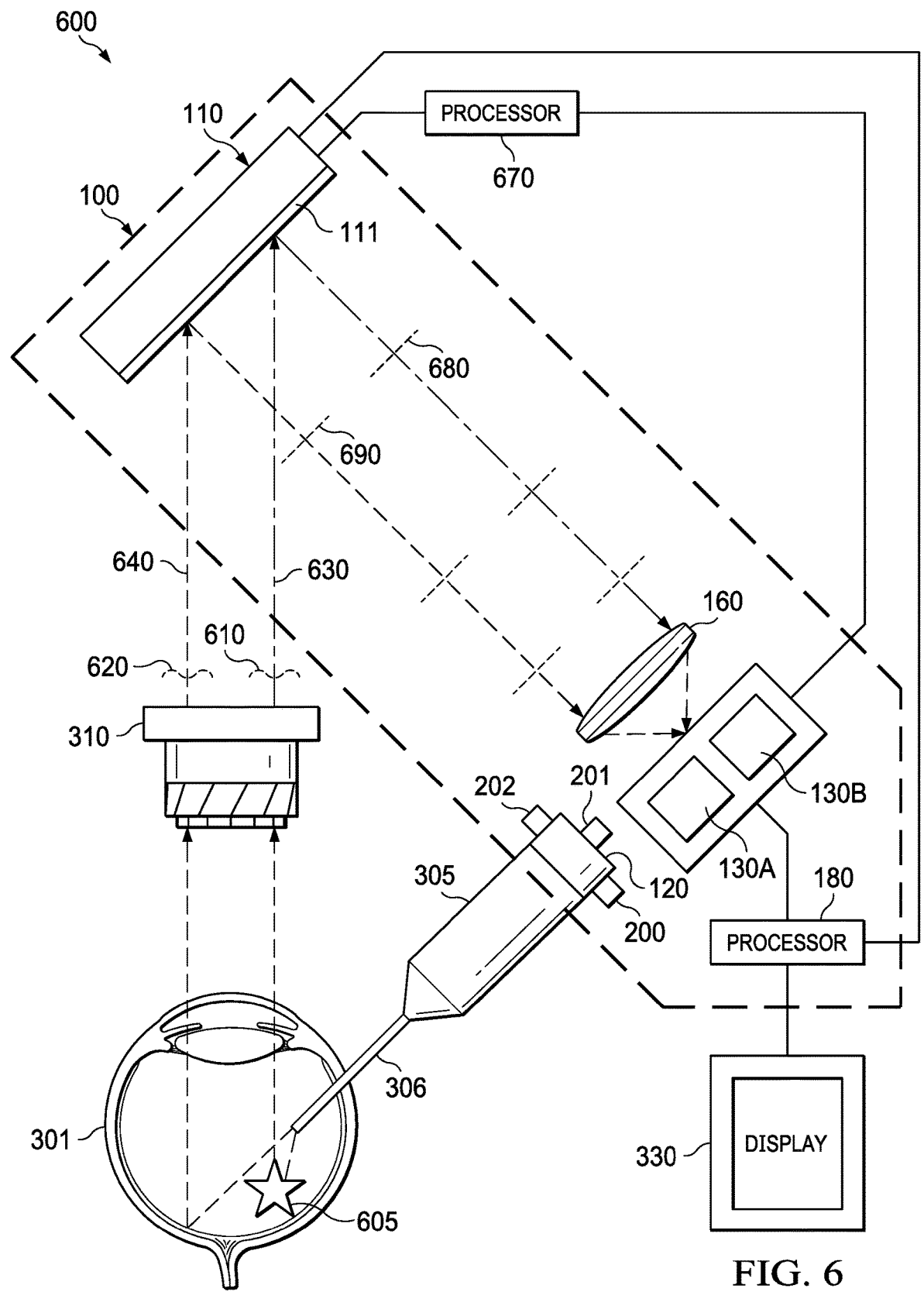
FIG. 6 is a schematic representation of an adaptive optics system, including an image reference system.

The adaptive optics system 100 to improve a digital image for vitreoretinal surgery may include image reference system 600 as depicted in FIG. 6. As shown in FIG. 6, image reference system 600 may include image reference 605, which may be a reference object with a known shape. Image reference 605 may be an object or surgical tool placed in eye 301. Image reference 605 may be a vitreous cutter, forceps, scissors, a pic, a scraper, a flex loop, a spatula, a MVR blade, a micro-cannula, or another surgical tool. If the shape of image reference 605 is not already known, it may also be placed outside of eye 301 in various poses before surgery commences to obtain non-aberrated image of image reference 605. This may allow image reference 605 to be used as an image reference when placed internally in eye 301 during surgery. Red, green, and blue light from the time sequential color system 120, which may be delivered by endoilluminator 305, may be reflected off image reference 605, may have wavefront distortion 610, and may take optical path 630. Red, green, and blue light from the time sequential color system 120 may also be reflected off eye 301, may have wavefront distortion 620, and may take optical path 640. Processor 670 may analyze wavefront distortion 610 in the digital image of image reference 605 provided by active pixel sensor arrays 130a and 130b and send instructions to wavefront correction system 110 to control and correct wavefront distortion 610 to corrected wavefront 680 to restore the aberrated image of image reference 605 to a non-aberrated image. These same instructions may be used to correct wavefront distortion 620 to corrected wavefront 690. Corrected wavefront 690 may be sent to active pixel sensor arrays 130a and 130b and may allow a digital image of eye 301 with improved resolution. Although processor 670 is depicted separately from processor 180 and active pixel sensor arrays 130a and 130b, they may be the same processor, or part of a single physical device, such as a single computer or a set of integrated circuits.

Figure 7:
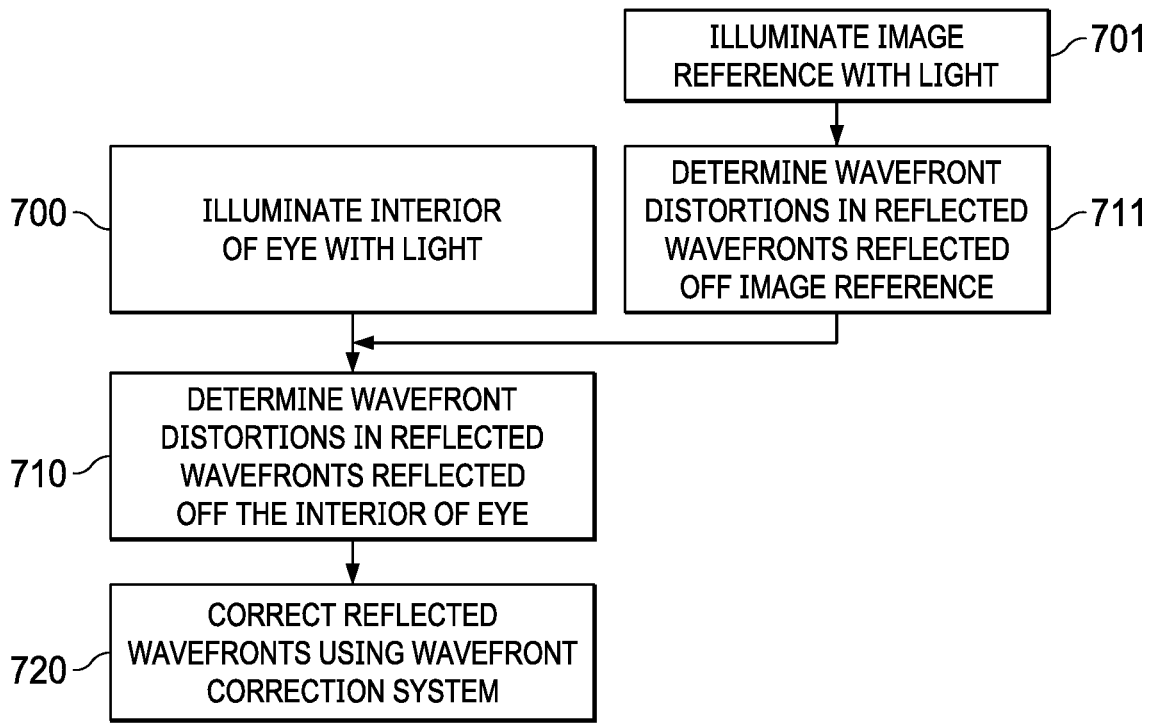
FIG. 7 is a flow diagram illustrating a method of correcting a wavefront distortion to improve a digital image for vitreoretinal surgery.

FIG. 7 presents a flow chart for a method of correcting a wavefront distortion to improve a digital image according to the disclosure. In step 700, light is used to illuminate an interior of an eye during surgery. The light may include a sequence of red, green, and blue light, such as that emitted by time sequential color system 120 and delivered by endoilluminator 305. The light is reflected off the interior of the eye to give a reflected wavefront of light. In step 710, the wavefront distortions of the reflected wavefront of light are determined. This step may involve concurrent use of an image reference system, such as image reference system 700. In step 701, light is used to illuminate an image reference during surgery. The light used to illuminate the image reference may include red, green, and blue light, such as that emitted by time sequential color system 120 and delivered by endoilluminator 305. The wavefront distortions of a reflected wavefront of light reflected off the image reference are determined in step 711. In step 720, a wavefront correction system, which may include a wavefront control structure that may be a SLM, a reflective LCoS-SLM, a transmissive LCoS-SLM, a deformable mirror, or any combination thereof, is used to correct the wavefront distortion for the reflected wavefront of light reflected off the interior of the eye, improving the image resolution of the digital image of the interior of the eye.

Figure 8:
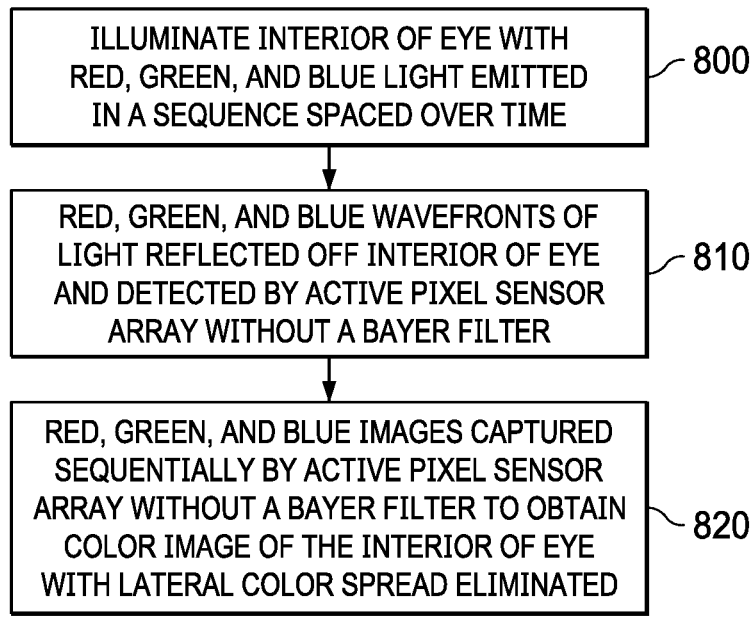
FIG. 8 is a flow diagram illustrating a method of eliminating lateral color spread in an adaptive optics system improve a digital image for vitreoretinal surgery.

FIG. 8 presents a flow chart for a method of eliminating lateral color spread and improving color rendition to improve a digital image for vitreoretinal surgery. In step 800, red light, green light, and blue light, such as that emitted by time sequential color system 120, are emitted in a sequence spaced over time to illuminate an interior of an eye during surgery. The red light, the green light, and the blue light are reflected off the interior of the eye in step 810 and may be detected by an active pixel sensor array. The active pixel sensor array may be an active pixel sensor array without a Bayer filter. In step 820, a red image, a green image, and a blue image are captured sequentially by the active pixel sensor array without a Bayer filter. The red image, the green image, and the blue image may be integrated in the viewer's visual cortex, or may be reformatted by an image processor to be displayed on an OLED display or head mounted display, to give a color image of the interior of the eye with lateral color spread eliminated. This method may improve the color rendition of the digital image of the interior of the eye.

Figure 9:
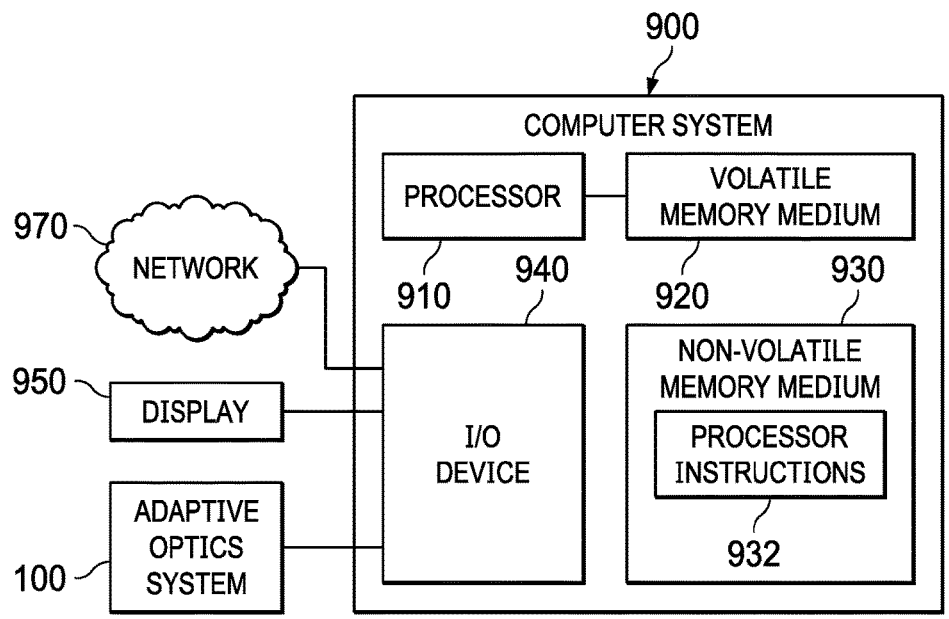
FIG. 9 is a schematic representation of a computer system, including an adaptive optics system.

Computer system 900 is depicted in FIG. 9. Computer system 900 may include a processor 910, a volatile memory medium 920, a non-volatile memory medium 930, and an input/output (I/O) device 940. Volatile memory medium 920, non-volatile memory medium 930, and I/O device 940 may be communicatively coupled to processor 910.

The term "memory medium" may mean a "memory", a "storage device", a "memory device", a "computer-readable medium", and/or a "tangible computer readable storage medium". For example, a memory medium may include, without limitation, storage media such as a direct access storage device, including a hard disk drive, a sequential access storage device, such as a tape disk drive, compact disk (CD), random access memory (RAM), read-only memory (ROM), CD-ROM, digital versatile disc (DVD), electrically erasable programmable read-only memory (EEPROM), flash memory, non-transitory media, or any combination thereof. As shown in FIG. 9, non-volatile memory medium 930 may include processor instructions 932. Processor instructions 932 may be executed by processor 910. In one example, one or more portions of processor instructions 932 may be executed via non-volatile memory medium 930. In another example, one or more portions of processor instructions 932 may be executed via volatile memory medium 920. One or more portions of processor instructions 932 may be transferred to volatile memory medium 920.

Processor 910 may execute processor instructions 932 in implementing at least a portion of one or more systems, one or more flow charts, one or more processes, and/or one or more methods described herein. For example, processor instructions 932 may be configured, coded, and/or encoded with instructions in accordance with at least a portion of one or more systems, one or more flowcharts, one or more methods, and/or one or more processes described herein. Although processor 910 is illustrated as a single processor, processor 910 may be or include multiple processors. One or more of a storage medium and a memory medium may be a software product, a program product, and/or an article of manufacture. For example, the software product, the program product, and/or the article of manufacture may be configured, coded, and/or encoded with instructions, executable by a processor, in accordance with at least a portion of one or more systems, one or more flowcharts, one or more methods, and/or one or more processes described herein.

Processor 910 may include any suitable system, device, or apparatus operable to interpret and execute program instructions, process data, or both stored in a memory medium and/or received via a network. Processor 910 further may include one or more microprocessors, microcontrollers, digital signal processors (DSPs), application specific integrated circuits (ASICs), or other circuitry configured to interpret and execute program instructions, process data, or both.

I/O device 940 may include any instrumentality or instrumentalities, which allow, permit, and/or enable a user to interact with computer system 900 and its associated components by facilitating input from a user and output to a user. Facilitating input from a user may allow the user to manipulate and/or control computer system 900, and facilitating output to a user may allow computer system 900 to indicate effects of the user's manipulation and/or control. For example, I/O device 940 may allow a user to input data, instructions, or both into computer system 900, and otherwise manipulate and/or control computer system 900 and its associated components. I/O devices may include user interface devices, such as a keyboard, a mouse, a touch screen, a joystick, a handheld lens, a tool tracking device, a coordinate input device, or any other I/O device suitable to be used with a system.

I/O device 940 may include one or more buses, one or more serial devices, and/or one or more network interfaces, among others, that may facilitate and/or permit processor 910 to implement at least a portion of one or more systems, processes, and/or methods described herein. In one example, I/O device 940 may include a storage interface that may facilitate and/or permit processor 910 to communicate with an external storage. The storage interface may include one or more of a universal serial bus (USB) interface, a SATA (Serial ATA) interface, a PATA (Parallel ATA) interface, and a small computer system interface (SCSI), among others. In a second example, I/O device 940 may include a network interface that may facilitate and/or permit processor 910 to communicate with a network. I/O device 940 may include one or more of a wireless network interface and a wired network interface. In a third example, I/O device 940 may include one or more of a peripheral component interconnect (PCI) interface, a PCI Express (PCIe) interface, a serial peripheral interconnect (SPI) interface, and an inter-integrated circuit (I2C) interface, among others. In a fourth example, I/O device 940 may include circuitry that may permit processor 910 to communicate data with one or more sensors. In a fifth example, I/O device 940 may facilitate and/or permit processor 910 to communicate data with one or more of a display 950 and adaptive optics system 100, among others. As shown in FIG. 9, I/O device 940 may be coupled to a network 970. For example, I/O device 940 may include a network interface.

Network 970 may include a wired network, a wireless network, an optical network, or any combination thereof. Network 970 may include and/or be coupled to various types of communications networks. For example, network 970 may include and/or be coupled to a local area network (LAN), a wide area network (WAN), an Internet, a public switched telephone network (PSTN), a cellular telephone network, a satellite telephone network, or any combination thereof. A WAN may include a private WAN, a corporate WAN, a public WAN, or any combination thereof.

Although FIG. 9 illustrates computer system 900 as external to adaptive optics system 100, adaptive optics system 100 may include computer system 900. For example, processor 910 may be or include processor 180.

Figure 10A:
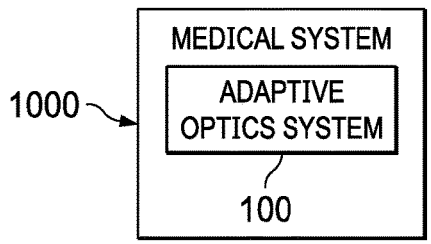
FIGS. 10A-10C are schematic representations of a medical system, including an adaptive optics system.
Figure 10B:
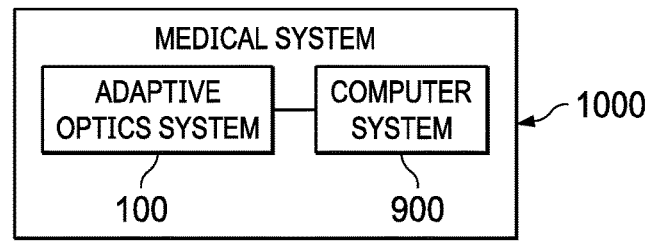
Figure 10C:
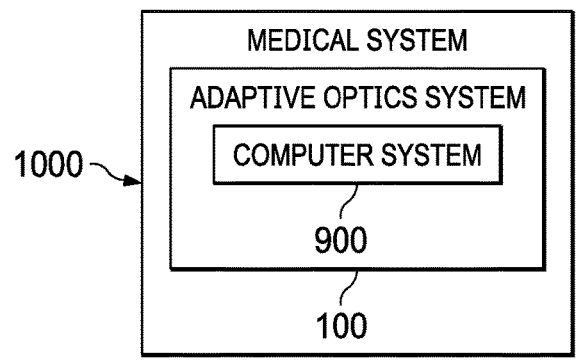

FIGS. 10A-10C illustrate examples of medical system 1000. As shown in FIG. 10A, medical system 1000 may include adaptive optics system 100. As illustrated in FIG.

10B, medical system 1000 may include adaptive optics system 100 and computer system 900. Adaptive optics system 100 may be communicatively coupled with computer system 900. As shown in FIG. 10C, medical system 1000 may include adaptive optics system 100, which may include computer system 900.

Figure 11:
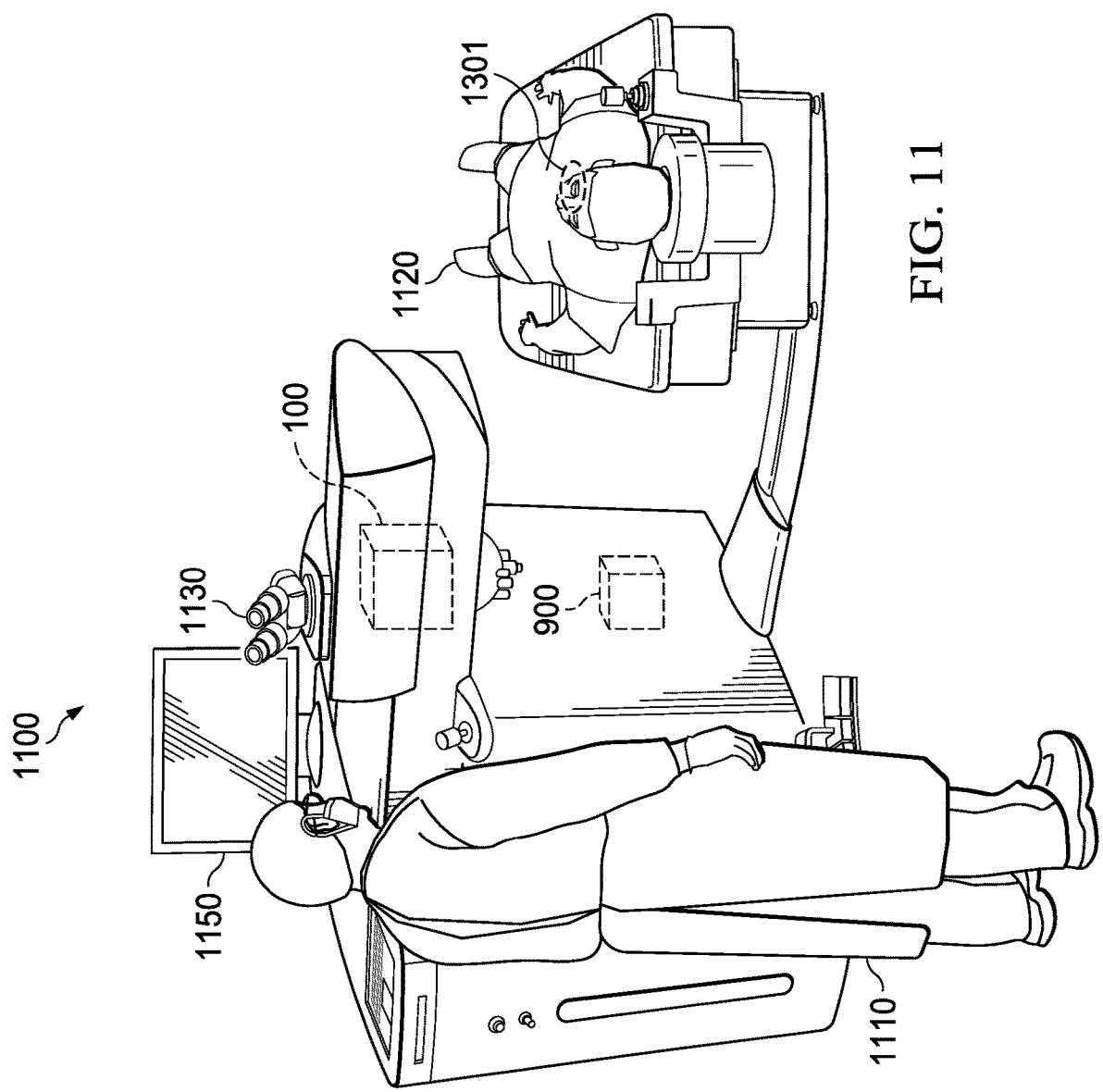
FIG. 11 is a schematic representation of a medical system, including an adaptive optics system, a surgeon, and a patient.

Adaptive optics system 100 may be used as a component of medical system 1100, as shown in FIG. 11. Medical system 1100 may include adaptive optics system 100. Medical system 1100 may include computer system 900. Surgeon 1110 may view a digital image of eye 1301 of patient 1120 on microscope integrated display (MID) 1130, display 1150, or any combination thereof. MID 1130, display 1150, or any combination thereof, may display an image of eye 1301 in which at least one wavefront of light reflected off the interior of eye 1301 is fully or partially corrected. The digital image of eye 1301 may have improved image resolution, improved image color rendition, improved image dynamic range, or any combination thereof, compared to a digital image of the eye captured without adaptive optics system 100. Medical system 1100 may include a processor; at least one active pixel sensor array coupled to the processor; a wavefront correction system coupled to the processor; an image reference system; and a memory medium, such as those in adaptive optics system 100 or image reference system 600. The memory medium may be coupled to the processor, and may include instructions that when executed by the processor, cause the medical system to utilize the image reference system to determine a wavefront distortion of a reflected wavefront of light reflected off the interior of eye 1301 of patient 1120. The memory medium may also include instructions that when executed by the processor, cause the medical system to utilize the wavefront correction system to correct the wavefront distortion of the reflected wavefront of light reflected off the interior of eye 1301.

Adaptive optics system 100, visualization system 300, visualization system 400, visualization system 500, image reference system 600, computer system 900, and medical system 1000, medical system 1100, and components thereof may be combined with other elements of visualization tools and systems described herein unless clearly mutually exclusive. For instance, the image reference and processor in image reference system 600 may be used with other visualization systems described herein.

The above disclosed subject matter is to be considered illustrative, and not restrictive, and the appended claims are intended to cover all such modifications, enhancements, and other embodiments which fall within the true spirit and scope of the present disclosure. For example, although an adaptive optics system is most commonly needed to improve a digital image during vitreoretinal surgery, if it were useful in another procedure, such as a purely diagnostic procedure not otherwise considered to be surgery, the systems and methods described herein may be employed.

The invention claimed is:

1. An adaptive optics system comprising:
a time sequential color system comprising a red light source, a green light source, and a blue light source operable to emit a sequence of red, green, and blue light spaced over a period of time;
at least one active pixel sensor array operable to detect light and send a signal to a processor, wherein the at least one active pixel sensor array is operable to detect each of the red, green, and blue light, and send a signal to the processor; and
a wavefront correction system comprising at least one wavefront control structure and the processor and operable to:
execute instructions on the processor to produce a digital image in which at least one wavefront distortion in the light detected by the active pixel sensor array is partially or fully corrected.

2. The adaptive optics system of claim 1 further comprising a plurality of active pixel sensor arrays.

3. The adaptive optics system of claim 1, wherein the wavefront control structure comprises a spatial light modulator (SLM), a liquid crystal on silicon spatial light modulator (LCoS-SLM), a transmissive LCoS-SLM, a reflective LCoS-SLM, a deformable mirror, or any combination thereof.

4. The adaptive optics system of claim 1, wherein the wavefront control structure comprises a phase-only SLM.

5. The adaptive optics system of claim 1, wherein the digital image is displayed on a digital display, a screen, a head up display, a head mounted display, or any combination thereof.

6. The adaptive optics system of claim 1, wherein the adaptive optics system is a component of NGENUITY®.

7. The adaptive optics system of claim 1 wherein the active pixel sensor array is a complementary metal-oxide-semiconductor (CMOS) monochrome sensor, a 4K monochrome CMOS sensor, a 1080P monochrome CMOS sensor, or any combination thereof.

8. The adaptive optics system of claim 1, further comprising an on-chip processor on the active pixel sensor array operable to implement a region of interest (ROI) gain control.

9. The adaptive optics system of claim 1, further comprising an amplitude-only SLM to implement a ROI gain control on the active pixel sensor array.

10. The adaptive optics system of claim 1, further comprising an image reference system.

11. The adaptive optics system of claim 10, wherein the image reference system comprises an image reference that is a surgical tool placed in an eye.

12. The adaptive optics system of claim 11, wherein the surgical tool is a vitreous cutter, forceps, scissors, a pic, a scraper, a flex loop, a spatula, a micro-vitreoretinal (MVR) blade, a micro-cannula, or any combination thereof.

13. The adaptive optics system of claim 1, wherein the time sequential color system comprises a red light emitting diode (LED), a green LED, and a blue LED pulsed in a sequence with an aggregate rate of 180 Hz or above.

14. The adaptive optics system of claim 1, wherein the time sequential color system comprises a red superluminescent light emitting diode (SLED), a green SLED, and a blue SLED pulsed in sequence with an aggregate rate of 180 Hz or above.

15. The adaptive optics system of claim 1, wherein the time sequential color system is delivered by an endoilluminator.

16. The adaptive optics system of claim 1, wherein the active pixel sensor array is an active pixel sensor array without a Bayer filter.

17. The adaptive optics system of claim 1, wherein the active pixel sensor array captures sequentially a red image, a green image, and a blue image.

18. A method of correcting a wavefront distortion to improve a digital image, the method comprising:
using an image reference system to determine a wavefront distortion of a reflected wavefront of light reflected off the interior of the eye; and using a wavefront correction system to correct the wavefront distortion of the reflected wavefront of light reflected off the interior of the eye.

\* \* \* \* \*